United States Patent [19]

Brown et al.

[11] Patent Number: 5,057,782
[45] Date of Patent: Oct. 15, 1991

[54] MICROWAVE SPECTROMETER

[75] Inventors: Ronald D. Brown, Mount Waverley; Peter D. Godfrey, Clayton; Jonathan G. Crofts, Vermont South, all of Australia

[73] Assignee: Monash University, Clayton, Australia

[21] Appl. No.: 555,391
[22] PCT Filed: Feb. 21, 1989
[86] PCT No.: PCT/AU89/00070
§ 371 Date: Aug. 16, 1990
§ 102(e) Date: Aug. 16, 1990
[87] PCT Pub. No.: WO89/08248
PCT Pub. Date: Sep. 8, 1989

[30] Foreign Application Priority Data
Feb. 26, 1988 [AU] Australia ............. PI6983

[51] Int. Cl.$^5$ ............................................. G01N 22/00
[52] U.S. Cl. ................................. 324/639; 324/636; 73/23.2; 73/23.41; 73/23.42
[58] Field of Search ............. 324/636, 639; 73/23.2, 73/23.41, 23.42

[56] References Cited
U.S. PATENT DOCUMENTS 3,889,182  6/1975  Easley et al. ................ 324/636
4,598,577  7/1986  Jowitt et al. ................. 73/23.2
4,607,521  8/1986  Saito et al. .................. 73/23.2
4,894,603  1/1990  Berger et al. ................ 324/639
4,896,097  1/1990  Berger et al. ................ 324/639

Primary Examiner—Hezron E. Williams
Assistant Examiner—William S. Francos
Attorney, Agent, or Firm—Finnegan, Henderson, Farabow, Garrett & Dunner

[57] ABSTRACT

A spectrometer for analyzing a sample substance which comprises a chamber (40) for supporting a sample to be analyzed. A gas drive circuit (42) communicates with the chamber (40) and the gas drive circuit (42) and chamber (40) are at least partly enclosed within a heated jacket (44). The gas flow through the gas circuit and chamber (40) entrains sample molecules in the flow and a nozzle (30) is provided to spray the gas flow and entrained molecules as a supersonic beam seeded with the molecules between a pair of plates (32 and 34) between which an electric field is created. The electrodes (32 and 34) comprise Stark electrodes. A microwave source (50) and a receiver (60) are arranged so that the source (50) produces a microwave beam which passes through the supersonic beam as the beam expands between the electrodes 32 and 34 which is detected by the detector 60. The detector 60 detects an absorption signal of the molecules which seed the supersonic beam.

5 Claims, 2 Drawing Sheets

MICROWAVE SPECTROMETER

BACKGROUND OF THE INVENTION

This invention relates to a spectrometer and in particular to a microwave spectrometer.

Microwave spectroscopy is known to measure changes in rotational energy of substances in the vapour state, it being possible to make measurements of each spectral line with such precision (at least to one part in 100,000 in the measurement of line frequencies) that accurate measurements of only a small number of lines (say 3 or 4) provides a unique fingerprint not shared by any other known chemical compound. The method of microwave spectroscopy therefore differs from virtually any other known analytical method in its uniqueness of identification.

The standard method of microwave spectroscopy has hitherto been limited to a small number of rather simple chemical compounds because the compound has had to be vaporized in order to study it whereas the great majority of chemicals of interest to business commerce, etc., such as pharmaceutical preparations, drugs etc., are involatile and normally thought of as not capable of being vaporized.

SUMMARY OF THE INVENTION

The object of this invention is to provide a spectrometer which is capable of use with at least some involatile substances.

The invention may be said to reside in a spectrometer for analyzing a sample substance, said spectrometer including:

(a) means for supporting the sample substance, (b) means for providing a flow of gas through or over said substance such that molecules of said substance are entrained in said gas flow, (c) nozzle means for receiving said gas flow entraining said molecules of the substance and for ejecting said flow of gas as a supersonic beam seeded with said molecules, (d) means for creating an electric field in the vicinity of said beam which is ejected by said nozzle means, (e) means for providing a source of electromagnetic radiation which passes through said beam in the vicinity of said electric field, and (f) means for detecting said electromagnetic radiation to thereby detect an absorption signal of the molecules which has been modulated in frequency by said electric field.

Since the substance to be studied is entrained in a gas flow which is ejected in the vicinity of an electric field, substances which are generally involatile can be analyzed with the invention since sufficient numbers of molecules can be entrained in a gas flow and reduced to the desired pressure and temperature during supersonic expansion of the beam ejected from the nozzle means to enable analysis to take place.

Preferably said means for creating an electric field comprises a pair of electrodes between which the beam and said electromagnetic radiation pass.

Preferably the electrodes are supported in a vacuum cavity and pump means is provided to create a vacuum in said cavity.

Preferably a cold trap is provided in said cavity to facilitate trapping of gas molecules in the gas flow to thereby facilitate maintenance of the vacuum in the cavity.

Preferably the means for supplying a gas flow together with the sample is heated by a heating means to cause some vaporization of the substance so that it can be more easily entrained in the gas flow and wherein the gas flow is maintained at a predetermined temperature by the heating means to maintain the substance in the vapour state not allowing deterioration of the substance.

BRIEF DESCRIPTION OF THE DRAWINGS

A preferred embodiment of the invention will be described with reference to the accompanying drawings, in which.

DETAILED DESCRIPTION OF THE INVENTION

Figure 1:
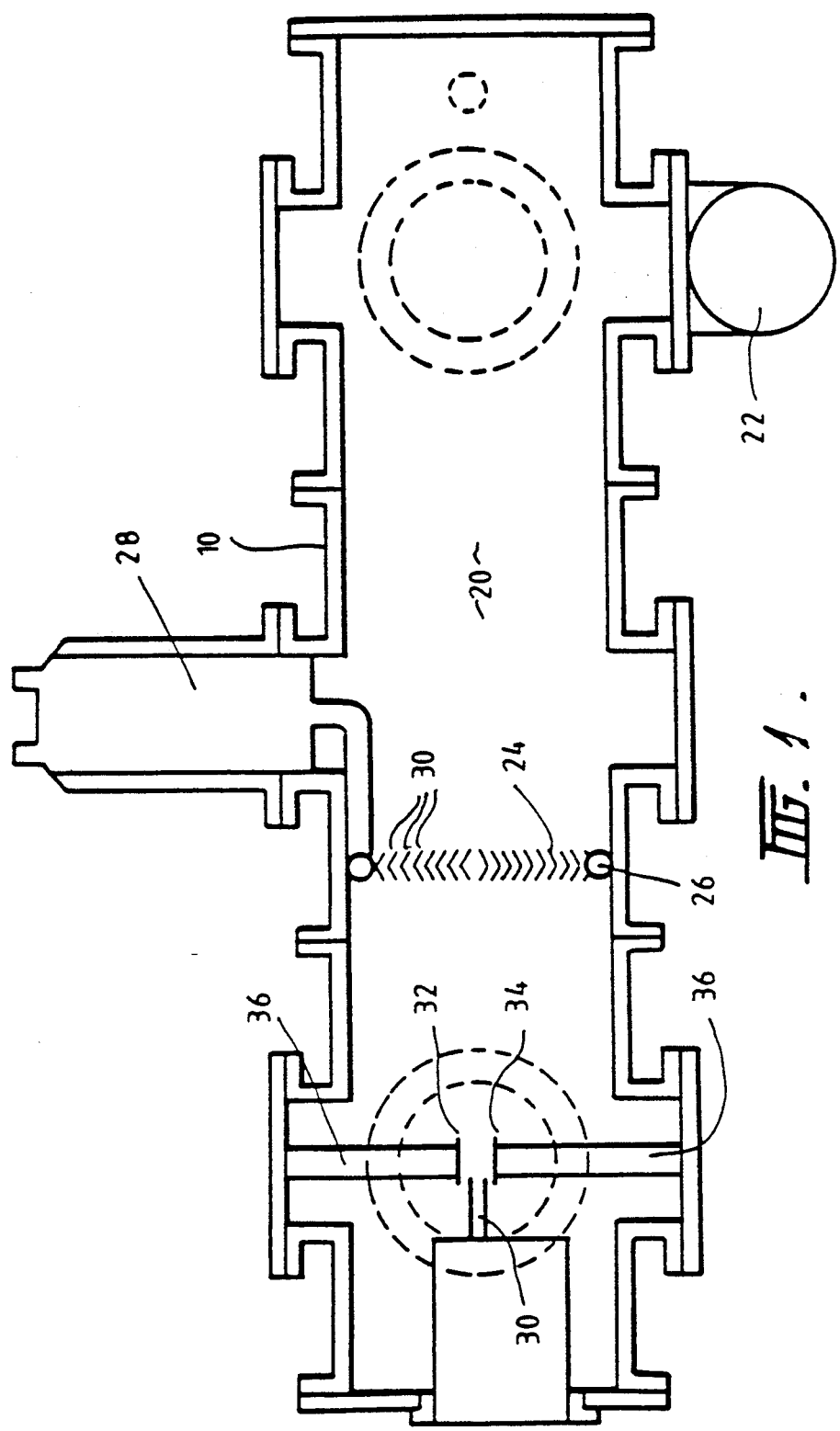
FIG. 1 is a view of a measurement cavity of a spectrometer according to the preferred embodiment of the invention.

With reference to FIG. 1 a generally cylindrical housing 10 is shown which defines a cavity 20 and is maintained at a low pressure (about 0.1 Pa) and preferably at a vacuum by a diffusion pump 22. The housing 10 also has a cold trap 24 which is preferably in the form of a Chevron Baffle cold trap which comprises a circular conduit 26 coupled to a supply 28 of liquid nitrogen. A plurality of baffles 30 extend across the circular conduit and are maintained at a very low temperature by conduction in view of the liquid nitrogen which circulates through the conduit 26.

Arranged at one end of the cavity 20 is a nozzle 30 which is directed between a pair of electrodes 32 and 34 which are supported by insulated supports 36.

Figure 2:
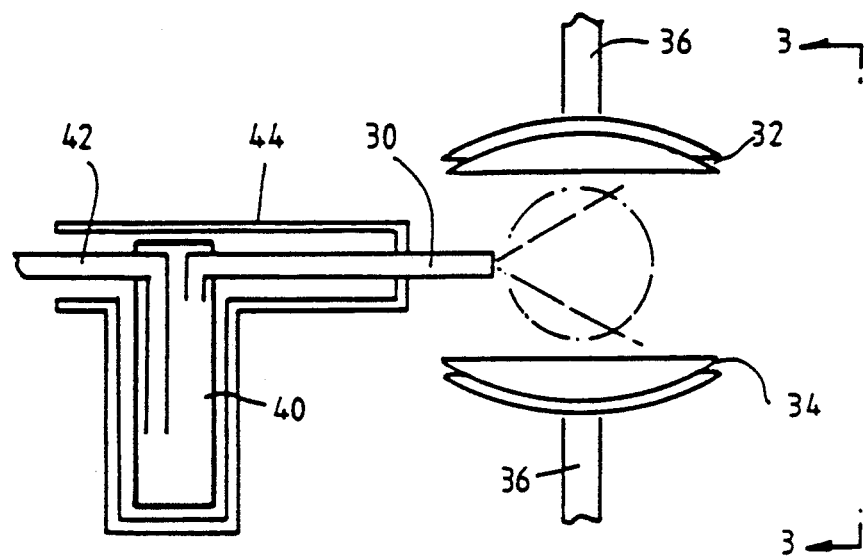
FIG. 2 is a view of the sample preparation device of the spectrometer.

As is best seen in FIG. 2 the nozzle 30 communicates with a sample chamber 40 which, in turn, communicates with a gas drive conduit 42. At least part of the gas drive conduit 42, the sample chamber 40 and the nozzle 30 are retained in a heated jacket 44. A supply of gas such as argon, helium, carbon dioxide, methane, cyclopropane etc., is coupled to the drive gas conduit 42 so that a continuous flow of gas can pass through the conduit 42 into the sample chamber 40 and then into the nozzle 30 to be sprayed from the nozzle 30 as a supersonic beam seeded with sample molecules. Since the sample chamber 40, the gas drive conduit 42 and the nozzle 30 are heated by the heating jacket 44, some molecules of the sample substance are vaporized to thereby facilitate entrainment into the gas flow passing from the conduit 42 into the nozzle 30. The heating of the chamber 40 and the nozzle 30 also maintains the molecules in the vaporized state and prevents them from condensing before being ejected as the supersonic beam from the nozzle 30. The temperature of the gas supplied through the conduit 42, sample and seeded gas flow through the nozzle 30 is carefully controlled to ensure that the sample substance does not deteriorate due to overheating. The supersonic beam seeded with sample molecules ejected from the nozzle 30 expands as it leaves the nozzle 30 as is shown by dotted lines in FIG. 2. The expansion takes place between the electrodes 32 and 34.

Figure 3:
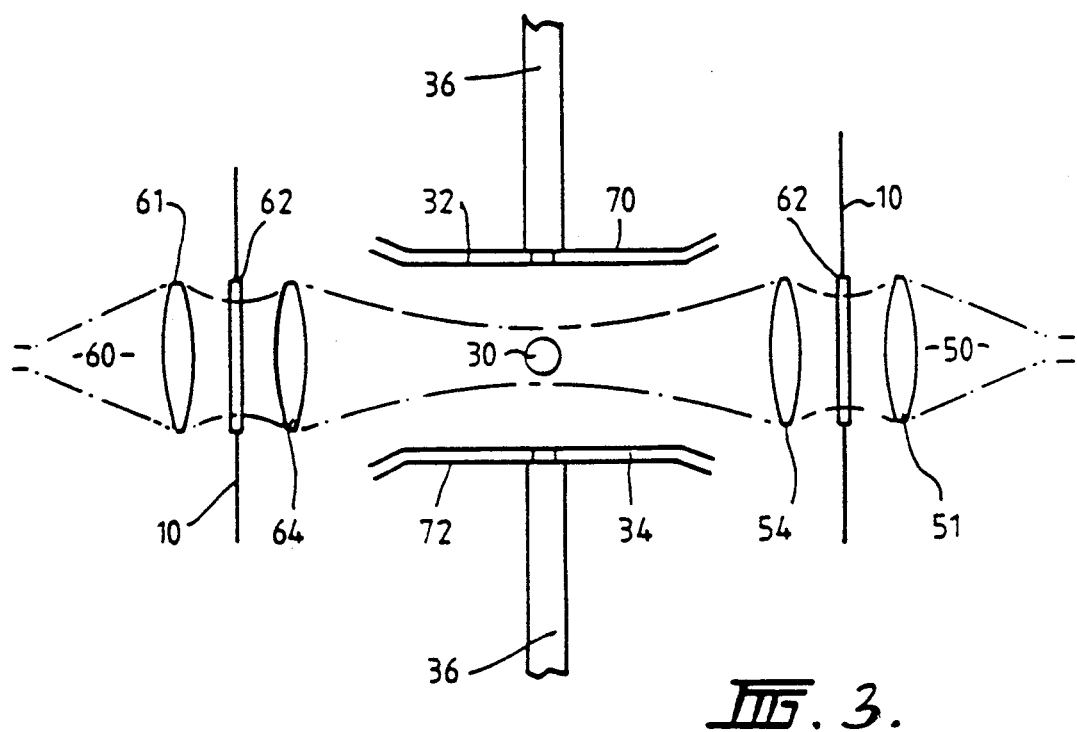
FIG. 3 is a view along the line 3—3 of FIG. 2.

As is best shown in FIG. 3, the electrodes 32 and 34 are preferably in the form of parallel discs of 100 mm diameter separated by a distance of 40 mm. Edges of the electrodes 32 and 34 are flared in the direction of a microwave beam source 50 and a microwave receiver 60 arranged exteriorly of the housing 10 to minimize microwave radiation reflections and to provide an effective modulation region between the electrodes 32 and 34.

The housing 10 which defines the cavity 20 is provided with teflon windows 62 through which a microwave beam can pass. The microwave source 50 and the receiver 60 may be provided with lenses 51 and 61 for controlling the beam passing through the windows 62 and further lenses 54 and 64 are provided inside the housing 10 to further control the microwave beam so that the beam passes through the expanding flow from the nozzle 30 and is concentrated in that region.

The lenses 51, 54, 61 and 64 together with the windows 62 are machined from PTFE and all surfaces are bloomed by machining circular grooves so as to achieve a half wave coating. Preferably the nozzle diameter in the nozzle 30 is about 550 micrometers and gas driving pressure is approximately 0.3 atmosphere with a sample throughput typically around 1 gram per hour.

In order to establish an electric field between the electrodes 32 and 34 one of the electrodes 32 or 34 is coupled to a positive square wave generator while its shield plate 70 or 72 is grounded and the other of the electrodes is coupled to a negative square wave generator and similarly its shield plate is grounded. The electrodes 32 and 34 generally comprise Stark electrodes and in order to establish electric field values adequate for Stark modulation and to overcome electric discharge problems associated with long-path gas breakdown, the shield plates 70 and 72 which are grounded are installed in close proximity to the electrodes 32 and 34. Preferably the shield plates 70 and 72 are separated from the electrodes 32 and 34 by a distance of about 2 mm. Closely spaced grounded shield plates are installed over all high-voltage surfaces within the vacuum chamber with the obvious exception of the front surfaces of the Stark modulation electrodes 32 and 34. With the electrodes 70 and 72 in place, the maximum Stark voltage supportable at operating pressures was increased from 1 kV to 3 kV above ground. A further doubling of the electric field available was achieved by the application of the opposite polarity positive square wave and negative square wave to the plates 32 and 34 which is applied by suitable generators (not shown). This provided symmetrical charging of the electrodes 32 and 34 which also tended to reduce distortion of the Stark field associated with the proximity of the nozzle assembly, which is at ground potential.

The cold trap 24 is most useful when the driving gas is carbon dioxide. The carbon dioxide solidifies and adheres to the cold trap upon contact which prevents circulation of carbon dioxide molecules in the cavity thereby further facilitating the maintenance of a vacuum in the cavity. If other driving gases are used, the cold trap provides a convenient baffle to prevent room temperature involatile solids contaminating the diffusion pump 22.

As previously explained, the conduit 42, sample chamber 40 and part of the nozzle 30 are heated by a heating jacket 44 which tends to vaporize some of the sample contained within the chamber 40 for entrainment into the gas flow. In order to increase contact between the gas flow and the sample, if the sample is a liquid, the chamber is preferably provided in a vertical orientation as is shown in FIG. 2. However, if the sample is a solid it is preferred that the chamber 40 be arranged in a horizontal direction to increase the surface area of the sample over which the gas flow passes. The heating jacket 44 maintains the gas flow and entrained sample molecules at a predetermined temperature which facilitates vaporization of some molecules of the sample and entrainment of those molecules into the gas flow. The predetermined temperature prevents condensation of the sample molecules before they are ejected from the nozzle and also must prevent decomposition or deterioration of the sample molecules. The supersonic jet which is ejected from the nozzle 30 expands immediately adjacent to the nozzle between the plates 32 and 34. The supersonic expansion reduces the pressure of the gas flow and also cools the sample molecules so increasing the population of molecules in the lower rotational energy state thereby simplifying and increasing the intensity of the spectrum which is monitored by the microwave beam from the source 50 which is detected by the receiver 60. The entrainment of the sample molecules in the gas flow ensures that sample molecules are delivered for analysis. Unless the molecules were entrained in the gas flow, the number of molecules delivered to the interaction region between electrodes 32 and 34, even if the sample is heated, would be insufficient to ensure adequate sensitivity for analysis. The electric field between the plates 32 and 34 changes the characteristic absorption frequency of the molecules, via the Stark effect, so modulating the absorption signal at a given frequency producing an AC signal from the receiver which can be easily amplified while maintaining excellent signal to noise ratio. The Stark effect also produces a characteristic pattern which is a further aid in uniquely identifying the molecule. The combination of the gas flow and entrainment of sample molecules in that flow, the electrodes 32 and 34 and the microwave source and receiver enables analysis of samples which were hitherto not capable of analysis in microwave spectrometers.

Preferably the microwaves are in the high frequency range (40 to 120 GHz) where absorption intensities will be optimal, to provide the best sensitivity. The operation of the spectrometer may be controlled by an on-line computer system which stores a data file of selected frequencies of the substances to be identified so that an operator can name the particular substance to be sought and the spectrometer then automatically selects frequencies and makes the sensitive search for the presence of the characteristic spectral lines.

Since modification within the spirit and scope of the invention may readily be effected by persons skilled within the art, it is to be understood that this invention is not limited to the particular embodiment described by way of example hereinabove.

The claims defining the invention are as follows:

1. A spectrometer for analyzing a sample substance, said spectrometer including:

(a) means for supporting the sample substance, (b) means for providing a flow of gas through or over said substance such that molecules of said substance are entrained in said gas flow, (c) nozzle means for receiving said gas flow entraining said molecules of the substance and for ejecting said flow of gas as a supersonic beam seeded with said molecules, (d) means for creating an electric field in the vicinity of said beam which is ejected by said nozzle means, (e) means for providing a source of electromagnetic radiation which passes through said beam in the vicinity of said electric field, and (f) means for detecting said electromagnetic radiation to thereby detect an absorption signal of the molecules which has been modulated in frequency by said electric field.

2. The spectrometer of claim 1 wherein said means for creating an electric field comprises a pair of electrodes between which the beam and said electromagnetic radiation pass.

3. The spectrometer of claim 2 wherein the electrodes are supported in a vacuum cavity and pump means is provided to create a vacuum in said cavity.

4. The spectrometer of claim 1 wherein a cold trap is provided in said cavity to facilitate trapping of gas molecules in the gas flow to thereby facilitate maintenance of the vacuum in the cavity.

5. The spectrometer of claim 1 wherein the means for supplying a gas flow together with the sample is heated by a heating means to cause some vaporization of the substance so that it can be more easily entrained in the gas flow and wherein the gas flow is maintained at a predetermined temperature by the heating means to maintain the substance in the vapour state while not allowing deterioration of the substance.

* * * * *